United States Patent
Khatib

(10) Patent No.: US 9,926,608 B2
(45) Date of Patent: *Mar. 27, 2018

(54) DETECTION OF LETHALITY GENE FOR IMPROVED FERTILITY IN MAMMALS

(71) Applicant: WISCONSIN ALUMNI RESEARCH FOUNDATION, Madison, WI (US)

(72) Inventor: Hasan Khatib, Fitchburg, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/958,951

(22) Filed: Dec. 4, 2015

(65) Prior Publication Data

US 2016/0130668 A1    May 12, 2016

Related U.S. Application Data

(62) Division of application No. 11/686,707, filed on Mar. 15, 2007, now abandoned.

(51) Int. Cl.
| | |
|---|---|
| *C12Q 1/68* | (2006.01) |
| *C12P 19/34* | (2006.01) |
| *C07H 21/02* | (2006.01) |
| *C07H 21/04* | (2006.01) |
| *A61D 19/02* | (2006.01) |
| *A61D 19/04* | (2006.01) |

(52) U.S. Cl.
CPC ........... *C12Q 1/6888* (2013.01); *A61D 19/02* (2013.01); *A61D 19/04* (2013.01); *C12Q 1/6883* (2013.01); *A01K 2227/101* (2013.01); *C12Q 2600/124* (2013.01); *C12Q 2600/156* (2013.01); *C12Q 2600/158* (2013.01)

(58) Field of Classification Search
CPC ............ A01K 67/027; A01K 2227/101; C12Q 1/6888; C12Q 1/6883; C12Q 2600/156
See application file for complete search history.

(56) References Cited

PUBLICATIONS

Juppner H. et al. Bone vol. 17, No. 2, Supplement, Aug. 1995:39S-42S.*
Pennisi E. Science; Sep. 18, 1998; 281, 5384, pp. 1787-1789.*
Hegele R.A. Arterioscler Thromb Vasc Biol. 2002;22:1058-1061.*

* cited by examiner

*Primary Examiner* — Stephen T Kapushoc
(74) *Attorney, Agent, or Firm* — Kening Li; Duane Morris LLP-DC

(57) ABSTRACT

Oligonucleic acid molecules comprising a SNP site at a position corresponding to position 7480 of the bovine signal transducer and activator of transcription (STAT5A) coding sequence (SEQ ID NO: 1). Also disclosed are an array or a kit comprising the same, a method for detecting the SNPs, a method for progeny testing of mammals, a method for increasing human and non-human mammal pregnancy rate in natural and artificial reproduction processes. Further provided are cattle breeding methods for improved milk production traits.

5 Claims, 1 Drawing Sheet

```
6781 accatcatcc tggatgacga gctgatccag tggaagcggc ggcagcagct ggcggggaac
6841 ggagggcccc ccgagggcag cctggatgtg ctacagtcct ggtaccaggg gtgggggcg
6901 gggaggggca ggcagcagag tggtgctgcc agctgctgtt tgcgcccacg tctacatgag
6961 cagctggctc cctctgtctg ggcgcgggtc ttatcccacc agtggtgtgt ttggtgctga
7021 caccggtgtc cctttctgtg cccctcccc tgggaggatg ctggggtggg gccaggtggc
7081 aaagtggcgc tcaggctggt tggacccag tcagtgtcgc tcctcctggg tgtttctctg
7141 gttttttgg aaggcagggc atctctgctg tgcccagtgc acaggcgagg tggctcgggc
7201 accaggcctt cctggggggtg gagctgggtg tgggccttgt ccccgcctgg gcgcytgcca
7261 gcttctggcc tggaggacgg gggtgaagcc cgtgtccttc ccttgggccc tggggctcgg
7321 gttcaggtgt gagaagttgg cggagattat ctggcagaac cggcagcaga tccgcagagc
          SEQ ID NO: 1
7381 cgagcacctc tgccagcagc tgcccatccc cggccccgtg gaggagatgc tggctgaggt
7441 caacgccacc atcactgaca tcatctcagc cctggtgacc aggtgactcc tggccacgcc
7501 ccgctcccat ctggttgccc tgggttgggg gcagcagggt ctttgcagat ggggagctct
7561 ggcttaaatc cttcagtttc tgcctcacac cctcctccca tccctctcca tccctgttg
7621 ctatggcctc ttgctgtcga cctcacccag tatttctcgt ggacactaca cgggcatttg
7681 tctcctgcaa ctcctttcag ctgctgagtt cctttactg cctcccttcc cgccagctcc
7741 cctgactcac agtggcccca ggagggtgg actgtccgca acccctcct tcacctgctc
7801 agcctggtgc aaggcaagcc tccccacgtg gaaggtgggg ccagagtcct gtcccctgaa
7861 gtgctcctgt cccttgtgtc tccgcagcac cttcatcatc gagaagcagc cccctcaggt
7921 cctgaagacc cagaccaagt tcgcggccac cgtgcgcctg ctggtgggtg ggaagctgaa
7981 cgtgcacatg aaccccccc aggtgaaggc caccatcatc agcgagcagc aggccaagtc
8041 actgctcaag aacgagaaca cccgcaagta tgctgcccgc tccttcatct gccctccccc
          SEQ ID NO: 2
8101 agctcagcct ctgctctgta gctggggtcc caggtgatga ggacacacgg ggcctcccac
8161 tctttgtcta gcattgcaat gacagatgac tctgtctgtc tgggggtatt cctcgcacac
8221 agagcaaatc aaggacttca ctattagggt gtcccaggat ctgtgctgag cactggcaca
8281 gtgctgggat ccacaccaaa cttggctcca tcacggccca acctttaggc tagcaggcag
8341 cagacgtgag aattgattac ttgctggcat gtgaaaagag agacactggg gcaccatgaa
8401 agtgggtcat ggaggggtg ggacagaatg acagctagtt tcaaggctgc ggggtgacta
8461 ggaggagatg gtgaacgggc gtggagaggg cagacgttcg ggcagagaga acacgggcct
8521 gtctggaaga ggagcagaca aagggcgtgg tggatggaga acccggggtg aggtcctggg
```

Partial sequence of the coding region for exons 5-19 of STAT5A (accession on AJ237937). The binding sites of the two PCR primers used to amplify the fragment (bold) for initial SNP identification are underlined, and the SNP position of 7480 is shaded. Positions are as originally labeled in the GenBank.

```
                        SEQUENCE LISTING

<160> NUMBER OF SEQ ID NOS: 3

<210> SEQ ID NO 1
   <211> LENGTH: 21
   <212> TYPE: DNA
   <213> ORGANISM: artificial
   <220> FEATURE:
   <223> OTHER INFORMATION: PCR PRIMER

<400> SEQUENCE: 1
gagaagttgg cggagattat c                                          21

<210> SEQ ID NO 2
   <211> LENGTH: 20
   <212> TYPE: DNA
   <213> ORGANISM: artificial
   <220> FEATURE:
   <223> OTHER INFORMATION: PCR PRIMER

<400> SEQUENCE: 2
gtgttctcgt tcttgagcag                                            20

<210> SEQ ID NO 3
   <211> LENGTH: 1800
   <212> TYPE: DNA
   <213> ORGANISM: Bos taurus

<400> SEQUENCE: 3
accatcatcc tggatgacga gctgatccag tggaagcggc ggcagcagct ggcggggaac    60
ggagggcccc ccgagggcag cctggatgtg ctacagtcct ggtaccaggg gtgggggcg    120 gggaggggca ggcagcagag tggtgctgcc agctgctgtt tgcgcccacg tctacatgag   180
cagctggctc cctctgtctg ggcgcgggtc ttatcccacc agtggtgtgt ttggtgctga   240
caccggtgtc cctttctgtg cccctcccc tgggaggatg ctggggtggg gccaggtggc    300
aaagtggcgc tcaggctggt tggacccag tcagtgtcgc tcctcctggg tgtttctctg    360 gttttttttgg aaggcagggc atctctgctg tgcccagtgc acaggcgagg tggctcgggc   420
accaggcctt cctggggggtg gagctgggtg tgggccttgt ccccgcctgg gcgcytgcca   480
gcttctggcc tggaggacgg gggtgaagcc cgtgtccttc ccttgggccc tggggctcgg    540
gttcaggtgt gagaagttgg cggagattat ctggcagaac cggcagcaga tccgcagagc    600
cgagcacctc tgccagcagc tgcccatccc cggccccgtg gaggagatgc tggctgaggt    660
```

```
caacgccacc atcactgaca tcatctcagc cctggtgacc aggtgactcc tggccacgcc      720
ccgctcccat ctggttgccc tgggttgggg gcagcagggt ctttgcagat ggggagctct      780
ggcttaaatc cttcagtttc tgcctcacac cctcctccca tccctctcca tccctgttg      840 ctatggcctc ttgctgtcga cctcacccag tatttctcgt ggacactaca cgggcatttg      900
tctcctgcaa ctcctttcag ctgctgagtt ccttttactg cctcccttcc cgccagctcc      960
cctgactcac agtggcccca gggagggtgg actgtccgca aaccctccct tcacctgctc     1020
agcctggtgc aaggcaagcc tccccacgtg gaaggtgggg ccagagtcct gtccctgaa      1080 gtgctcctgt cccttgtgtc tccgcagcac cttcatcatc gagaagcagc ccctcaggt      1140 cctgaagacc cagaccaagt tcgcggccac cgtgcgcctg ctggtgggtg ggaagctgaa     1200
cgtgcacatg aaccccccc aggtgaaggc caccatcatc agcgagcagc aggccaagtc     1260
actgctcaag aacgagaaca cccgcaagta tgctgcccgc tccttcatct gccctccccc     1320
agctcagcct ctgctctgta gctggggtcc caggtgatga ggacacacgg ggcctcccac     1380
tctttgtcta gcattgcaat gacagatgac tctgtctgtc tgggggtatt cctcgcacac     1440
agagcaaatc aaggacttca ctattagggt gtcccaggat ctgtgctgag cactggcaca     1500
gtgctgggat ccacaccaaa cttggctcca tcacggccca acctttaggc tagcaggcag     1560
cagacgtgag aattgattac ttgctggcat gtgaaaagag agacactggg gcaccatgaa     1620
agtgggtcat ggaggggtg ggacagaatg acagctagtt tcaaggctgc ggggtgacta      1680
ggaggagatg gtgaacgggc gtggagaggg cagacgttcg ggcagagaga acacgggcct     1740
gtctggaaga ggagcagaca aagggcgtgg tggatggaga acccgggtg aggtcctggg      1800
```

DETECTION OF LETHALITY GENE FOR IMPROVED FERTILITY IN MAMMALS

This invention was made with government support under 05-CRHF-0-6055 awarded by the USDA/NIFA. The government has certain rights in the invention.

FIELD OF THE INVENTION

The present invention relates to methods and compositions for detecting a lethality allele in an animal, especially a mammal, and for improving fertility or increasing reproductive performance of the animal. The present invention further relates to methods and compositions for improving milk production of dairy cattle.

BACKGROUND OF THE INVENTION

It is highly desirable in many contexts that reproductive performance in mammals be improved or enhanced. For example, in farm animals, increased pregnancy rate and/or increased numbers of live offspring often would increase profitability. In meat-producing animals, increased litter size and birth or hatching rates improve the overall efficiency and profitability of a farm operation. Embryonic survival is directly relevant in avian species to improved hatching rates and for aquatic species to improved survival rate per spawn. Swine litter size would be positively influenced by the elimination of conditions that are lethal for developing embryos. Improved survival spreads the hatchery or piggery cost over a larger number of offspring, for example day-old chicks, post larvae shrimp, or piglets, and thus reduces the unit cost of production.

In milk producing animals, aside from the inherent value of young animals, periodic pregnancy and the resultant early lactation period are necessary or desirable for the animal to have steady and high milk yield. Tremendous efforts, such as systematic animal breeding programs and artificial insemination, have been and continue to be invested in ensuring that the animals have high and sustained productivity, and that the milk produced is of high quality or has desired composition.

While modern cattle breeding technologies have increased consistency of herd quality or performance and generally achieved increased milk yield, many studies have reported a decrease in fertility in dairy cows. Cows with the highest milk production have the lowest fertility performance. For example, it is well known that infertility is the major reason for culling cows, and it is estimated that in the UK alone, over 17,000 cows are culled every year due to infertility or reproductive failure (Genus Breeding, UK). Epidemiological studies suggest that, in addition to milk production, other factors such as increasing levels of inbreeding are probably decreasing reproductive efficiency in the dairy herd. The first-service conception rate declined approximately from 65% in 1951 to 40% in 1996 (Lucy, 2001, Reproductive loss in high-producing dairy cattle: where will it end? J Dairy Sci. 84:1277-93.). A large number of "normal embryos" in dairy cattle are found to undergo early embryonic death, but there is currently no explanation for such early embryo death. Reducing embryonic loss and achieving high rates of conception in dairy cattle would change the way we manage the lactation cycle (Lucy, 2001, supra).

The conception rate for cattle in the U.S. at first artificial insemination (AI) has also been decreasing for many years, and according to one report it decreased by 0.45% per year over a 20-year period (Butler and Smith, 1989, J. Dairy Sci. 72:767-83.). There was an increase in the number of AIs required for conception from 1.75 to more than 3 over a period of 20 years (Lucy, 2001, supra). Conception rates in large commercial herds stand at only 35-40% for mature cows. A similar need for improved reproductive performance exists with regard to many other farm animals such as swine, equine, sheep and goat.

In humans, infertility or low fertility plagues a significant portion of the population. It has been reported that in Western countries, about 10-15% of couples experience some difficulty with fertility (Evers, 2002, Female subfertility. Lancet 2:151-159.) Many couples suffering from impaired reproductive ability go to great effort and expense to successfully give birth to a child. The economic and emotional costs of embryonic mortality are significant, and a better understanding of its causes and improved methods for managing it are needed.

Infertility or low reproductive performance in animals, however, is presently poorly understood although it is known that there are many contributing factors, both genetic and environmental. It is nevertheless readily recognized that a genetic factor that causes the death of the embryo will be a major factor.

Lethal genes have been suggested as a cause of embryonic death and, if present, could cause failures in recurrent inseminations. However, lethal genetic factors or lethality genes if dominant, cannot survive in a population. Consequently, little is known about these lethal genetic factors. Identification and characterization of lethality genes would allow animal breeders, farmers and doctors to better understand low fertility, selectively improve the chances of success in animal breeding, develop strategic plans for improved fertility based on the genetics of parents and help eliminate these lethal factors from the population and improve overall reproductive performance in mammals.

As natural selection favors survival and reproduction of the more advantageous variants and elimination of the less advantageous variants, and an allele that confers lethality, even though recessive, generally decreases reproductive fitness of the individual carrying the lethality alleles. These recessive lethal alleles will eventually disappear from the population, unless it is otherwise selected for. Unnatural prevalence of a lethal allele, that is, at a frequency higher than predicted, indicates that it is favored by the condition under which the population is selected or propagated. Thus, if an allele is recessively lethal (reproductively disadvantaged), yet confers certain desirable production traits (for example, in the case of dairy cattle, milk yield or milk quality), this allele may be favored by breeding programs and persist in incidences higher than expected under natural selection conditions, even though its identity or phenotypic characteristics are not known. Insight about the exact nature of the phenotypic characteristics of recessive lethal alleles will be invaluable in assisting animal breeders in balancing reproductive performance with the animal's productive traits, and in achieving optimal economic outcome.

SUMMARY OF THE INVENTION

It has now been surprisingly discovered that a single nucleotide polymorphism (SNP) in the STAT5 gene is responsible for early embryo death in many animals including mammals, especially dairy cattle. Embryos homozygous with regard to a form of this SNP die at very early stages. This is believed to be the first reported gene associated with lethality at an early developmental stage in mammals. It is further discovered that in dairy cattle, an individual heterozygous with regard to this allele produces higher milk yield, as well as higher milk fat content and protein content when compared to individuals homozygous of the non-lethal allele.

In one embodiment, the present invention provides an isolated single or double stranded nucleic acid molecule comprising a polymorphic site at a position corresponding to position 7480 of exon 8 of the bovine Signal Transducer and Activator 5A (STAT5A) coding sequence (SEQ ID NO: 3), wherein position 7480 is either cytosine (the C allele) or guanine (the G allele), and at least about 9 contiguous nucleotides of SEQ ID NO: 3 adjacent to the polymorphic site. Preferably, the nucleic acid molecule comprises at least about 10, or at least about 15, or at least about 20 contiguous nucleotides adjacent to the polymorphic site. The isolated nucleic acid molecule of the present invention in certain circumstances preferably comprises not more than about 150 nucleotides, or not more than about 100 nucleotides, or not more than about 50 nucleotides.

In a preferred embodiment, the polymorphic site is within 4 nucleotides of the center of the nucleic acid molecule according to the present invention, or at the center of the nucleic acid molecule, or is at the 3'-end of the nucleic acid molecule.

In another embodiment, the present invention provides an array of nucleic acid molecules comprising the above isolated nucleic acid molecule supported on a substrate. The array may further comprise one or more markers in linkage disequilibrium with the polymorphic site. In another embodiment, the present invention provides a kit comprising a nucleic acid molecule described above, and a suitable container.

In another embodiment, the present invention provides a method for detecting single nucleotide polymorphism (SNP) on STAT5A coding region in an animal cell, the method comprising determining the identity of a nucleotide at a position corresponding to position 7480 of exon 8 of bovine STAT5A coding sequence (SEQ ID NO: 3) of the cell. The animal may be a mammalian, avian or aquatic species, and the animal cell may be an adult cell, an embryo cell, a sperm, an egg, a fertilized egg, or a zygote. Preferably, the mammal is bovine.

In a preferred embodiment, the identity of the nucleotide is determined by sequencing nucleic acid molecule, or a relevant fragment thereof, isolated from the cell. The nucleic acid molecule may be isolated from the cell via amplification by the polymerase chain reaction (PCR) of genomic DNA of the cell, or by RT-PCR of the mRNA of the cell.

In another preferred embodiment, the identity of the nucleotide is determined by hybridizing a suitable probe to a nucleic acid preparation from the cell, wherein the probe is preferably labeled with a detectable label.

In a further embodiment, the identity of the nucleotide is determined by an invasive signal amplification assay.

Preferably, the sequence of both copies of the polymorphic genetic locus in the cell is determined.

In another embodiment, the present invention provides a method wherein the identity of the SNP site in the cell is determined based on the genotypes of the parents, the genotypes of a daughter, or both.

In another embodiment, the present invention provides a method for determining whether an individual animal is suitable as a gamete donor for natural mating, artificial insemination or in vitro fertilization procedure, the method comprising determining the allele identity of the SNP site according to the present invention, or of an allele in linkage disequilibrium with the SNP site, and selecting as a gamete donor only an individual whose genotype is homozygous with regard to the C allele at the SNP site, or homozygous with regard to an allele in linkage disequilibrium with the C allele. Preferably, the animal is selected from the group consisting of cattle, swine, equine, dog, sheep and goat.

In another embodiment, the present invention provides a method of selecting an embryo for planting in a uterus, the method comprising determining identify of the nucleotide at a position corresponding to position 7480 of STAT5A (SEQ ID NO: 3) of the embryo while preserving the viability of the embryo, and selecting for planting only an embryo whose genotype is CC homozygous at the position. Preferably, multiple ovulation and embryo transfer (MOST) is used to generate multiple fertilized eggs.

In another embodiment, the present invention provides a method for increasing successful pregnancy rate of a non-human animal, comprising selecting a male or a female mammal for breeding purposes that are CC homozygous at a position correspond to position 7480 of exon 8 of bovine STAT5A gene (SEQ ID NO: 3). Preferably, both the male and female parents are selected to be CC homozygous. The female mammal may be in vitro fertilized.

In another embodiment, the present invention provides a method for increasing pregnancy rate and reducing multiple pregnancy rate in a human assisted reproductive technologies (ART) procedure, the method comprising genotyping, via pre-implantation genetic diagnosis, the genotype of embryos to be planted with regard to the nucleotide corresponding to position 7480 of exon 8 of bovine STAT5A gene (SEQ ID NO: 3), and planting not more than 3 embryos which are homozygous CC with regard to the position.

In yet another embodiment, the present invention provides a method for determining whether an individual dairy cattle is suitable as a gamete donor for a natural mating, artificial insemination or in vitro fertilization procedure, the method comprising determining allele identify of the SNP site according to the present invention, or of an allele in linkage disequilibrium with the SNP site, and selecting as gamete donor an individual whose genotype is heterozygous at the SNP site, or heterozygous with regard to a locus in linkage disequilibrium with the C allele. Preferably, an individual having CC genotype at the SNP site is selected to mate with an individual with a CG genotype. Still more preferably, gametes from the CG individual and the CC individual are used in artificial insemination, or in in vitro fertilization, or in multiple ovulation and embryo transfer procedure.

In another embodiment, the present invention provides a method of selecting a dairy cattle embryo for planting in a uterus, the method comprising determining the identity of the nucleotide at a position corresponding to position 7480 of bovine STAT5A (SEQ ID NO: 3) of the embryo while preserving the viability of the embryo, and selecting for planting only an embryo whose genotype is CG heterozygous at the position.

BRIEF DESCRIPTION OF THE DRAWINGS

FIG. 1 shows the partial sequence of the coding region for exons 5-19 of STAT5A (accession no. AJ237937) (SEQ ID NO: 3). The binding sites of the two PCR primers used to amplify the fragment (bold) for initial SNP identification are underlined, and the SNP position of 7480 is shaded. Positions are as originally labeled in the GenBank.

DETAILED DESCRIPTION OF THE INVENTION

The Signal Transducer and Activator (STAT) proteins are known to play an important role in cytokine signaling pathways. The proteins are transcription factors that are specifically activated to regulate gene transcription when cells encounter cytokines and growth factors, hence they act as signal transducers in the cytoplasm and transcription activators in the nucleus (Kisseleva et al., Signaling through the JAK/STAT pathway, recent advances and future challenges. Gene 285: 1-24 (2002)). Binding of factors such as cytokines and growth factors to cell-surface receptors leads to receptor autophosphorylation at a tyrosine, the phosphotyrosine being recognized by the STAT SH2 domain, which mediates the recruitment of STAT proteins from the cytosol and their association with the activated receptor. The STAT proteins are then activated by phosphorylation via members of the JAK family of protein kinases, causing them to dimerize and translocate to the nucleus, where they bind to specific promoter sequences in target genes. In mammals, STATs comprise a family of seven structurally and functionally related proteins: Stat1, Stat2, Stat3, Stat4, Stat5a, Stat5b, and Stat6.

Signaling through the JAK/STAT pathway is initiated when a cytokine binds to its corresponding receptor. This leads to conformational changes in the cytoplasmic portion of the receptor, initiating activation of receptor associated members of the JAK family of kinases. The JAKs, in turn, mediate phosphorylation at the specific receptor tyrosine residues, which then serve as docking sites for STATs and other signaling molecules. Once recruited to the receptor, STATs also become phosphorylated by JAKs, on a single tyrosine residue. Activated STATs dissociate from the receptor, dimerize, translocate to the nucleus and bind to members of the GAS (gamma activated site) family of enhancers.

The seven STAT proteins identified in mammals range in size from 750 and 850 amino acids. The chromosomal distribution of these STATs, as well as the identification of STATs in more primitive eukaryotes, suggest that this family arose from a single primordial gene. STATS share structurally and functionally conserved domains (see e.g. Chen et al., Crystal structure of a tyrosine phosphorylated STAT-1 dimer bound to DNA. Cell 93: 827-839 (1998)).

The STAT5A protein is also known as the mammary gland factor (MGF). MGF knockout female mice failed to lactate. The encoding genomic region is about 19,517 bp long, and has 19 exons. The bovine sequence is known and is publicly available in the GenBank (accession number AJ242522 for exons 1-4 and AJ237937 for exons 5-19. The protein was initially identified in the mammary gland as a prolactin-induced transcription factor. STAT5A is a member of the IFN-tau and placental lactogen (PL) signaling pathway. The uterus is exposed to IFN-tau, PL, as well as others hormones including estrogen, progesterone, and placental growth hormone. Mediated by prolactin receptor (PRLR) homodimers, and perhaps by PRLR and growth hormone receptor (GHR) heterodimers, PL stimulates the formation of STATS homodimers, which in turn induce the transcription of bovine uterine milk protein (UTMP) and osteopontin (OPN) genes (see e.g. Spencer T. E. and Bazer F. W. 2002. Biology of progesterone action during pregnancy recognition and maintenance of pregnancy. Front. Biosci. 1, d1879-98; Stewart M. D., Choi Y., Johnson G. A., Yu-Lee L. Y. et al. 2002. Roles of Stan, Stat2, and interferon regulatory factor-9 (IRF-9) in interferon tau regulation of IRF-1. Biol Reprod. 66, 393-400; Spencer T. E. and Bazer F. W. 2004. Conceptus signals for establishment and maintenance of pregnancy. Reprod Biol Endocrinol. 2, 49). The UTMP gene is known to affect milk production traits in cattle. The OPN protein was first described in 1979 as a protein associated with malignant transformation, and has been intensively studied in human, mouse, and sheep. It has been suggested that human OPN has various roles in cell adhesion, chemotaxis, cell survival, tissue remodeling, regulation of inflammation, fetal growth and development, and in initiating and maintaining pregnancy (Denhardt et al. 2001, Osteopontin as a means to cope with environmental insults: regulation of inflammation, tissue remodeling, and cell survival. J Clin Invest. 107:1055-1061; Johnson et al., 2003. Osteopontin: roles in implantation and placentation. Biol Reprod. 69:1458-1471).

STAT5A and STAT5B from the same species share about 96% sequence similarity at the amino acid level. The sequence homology among STATS proteins from different animal species is high, as shown in Table 1, which summarizes the sequence similarity of STAT5 proteins among various species when compared to the bovine sequence. Table 1 also makes clear that the sequence homology among mammalian species is especially high.

TABLE 1

Sequence similarity among STAT5A proteins

| Species | Sequence similarity to Bovine Sequence Accession No. CAB52173 (%) |
| --- | --- |
| Canine | 97 |
| Sus Scrofa | 96 |
| Human | 96 |
| Mouse | 96 |
| Rattus | 95 |
| Ovies aries | 94 |
| Gallus gallus | 90 |
| Danio rerio | 79 |
| Takifugo rubripes | 79 |
| Xenopus laevis | 87 |

The present inventor has identified a single nucleotide polymorphism (SNP) in STAT5A that is associated with early embryo death in animals. The term "polymorphism" as used herein refers to the occurrence of two or more alternative genomic sequences or alleles between or among different genomes or individuals. "Polymorphic" refers to the condition in which two or more variants of a specific genomic sequence can be found in a population. A "polymorphic site" is the locus at which the variation occurs. A polymorphic site generally has at least two alleles, each occurring at a significant frequency in a selected population. A polymorphic locus may be as small as one base pair, in which case it is referred to as single nucleotide polymorphism (SNP). The first identified allelic form is arbitrarily designated as the reference form, and other allelic forms are designated as alternative or variant alleles. The allelic form occurring most frequently in a selected population is sometimes referred to as the wild type form. Diploid organisms may be homozygous or heterozygous for an allelic form. A biallelic polymorphism has two forms, and a triallelic polymorphism has three forms, and so on.

Polymorphisms may provide functional differences in the genetic sequence, through changes in the encoded polypeptide, changes in mRNA stability, binding of transcriptional and translation factors to the DNA or RNA, and the like. Polymorphisms are also used to detect genetic linkage to phenotypic variation.

SNPs have gained wide use for the detection of genetic linkage recently. SNPs are generally biallelic systems, that is, there are two alleles that an individual may have for any particular SNP marker.

The SNP associated with early embryo death according to the present invention is located on STAT5A, at a position corresponding to position 7480 on exon 8 of the bovine sequence (GenBank accession number AJ237937) (see FIG. 1). It has been discovered that at this position, the predominant allele is cytosine (C), and the other allele is guanine (G), and that homozygote GG genotype is lethal and does not exist in the population.

It is well-known to those ordinarily skilled in the art that the STAT5A genes in all animal species are derived from a common ancestor, which is reflected in the high DNA sequence similarity of the gene among these species. The nucleotide sequences of different animal species can be easily aligned, using widely available sequence comparison/alignment tools (e.g. Altschul, et al., 1990, "Basic local alignment search tool." J. Mol. Biol. 215:403-410), allowing maximum number of identical nucleotides on sequences from different animals to be positioned and correspond to each other. Similar alignment can be done based on the amino acid sequences encoded by the nucleic acid sequence. In many instances, appropriate gaps and insertions, determined by widely accepted computer algorithm, are introduced to allow for genetic deletions or insertions that are believed to have occurred during the evolutionary history of the genes. Accordingly, by a "corresponding" nucleotide position, as used in the present invention, is meant a nucleotide position that is identified using the nucleotide sequence alignment methodologies well-known in the art, based on a reference sequence, e.g. the bovine STAT5A sequence.

Using two PCR primers, STAT7 and STAT8, the inventor amplified and sequenced a 712-bp fragment from more than 2100 bovine samples from different cattle breeds (Holstein, Jersey, Brown Swiss, Bison bison, and Bos indicus). STAT7 is located on exon 8, and STAT8 is located on exon 9. The sequences of the two primers are: STAT7: 5'-GAGAAGT-TGGCGGAGATTATC-3' (SEQ ID NO:1) and STAT8: 5'-GTGTTCTCGTTCTTGAGCAG-3' (SEQ ID NO: 2). It was found that at the SNP position (7480), the predominant allele was cytosine (C), and the other allele was guanine (G), with about 70% CC homozygote, and about 30% CG heterozygote. No cattle GG homozygote was found. This lead to the conclusion that the GG homozygote is lethal and does not exist in the population.

The samples include semen samples from more than 1200 bulls and 1100 blood samples from Holstein cows. The 1100 blood samples were obtained from a University of Wisconsin (UW) daughter design resource population, consisting of 12 sire families. The sires used to create this population were chosen from a large number of candidate bulls with large numbers of daughters in production in the year 2000. Criteria for the final selection of the 12 bulls included large numbers of daughters in production, in total and separately in lactations 1, 2 and 3, and relatively low pedigree relationships among the chosen bulls in order to more broadly sample the chromosomes of the U.S. Holstein population. The 1200 semen samples were obtained from 30 half-sib families with a granddaughter design. Genomic DNA was extracted from semen samples by standard methods using proteinase K and phenol/chloroform extraction, and from blood samples using GFX Genomic Blood DNA Purification Kit (Amersham Biosciences, Piscataway, N.J.). The DNA concentration was measured using a spectrophotometer (Ultraspec 2100; Amersham Biosciences).

Cattle fetuses at 55-125 days were similarly genotyped and none was found to be GG homozygous, supporting the correlation between the GG homozygote and lethality. Fetuses were obtained from a local slaughterhouse. DNA was extracted from fetal tissues and genotyped with STAT5 gene.

Similar results were obtained from sheep samples. Two half-sib sheep families were genotyped, where the two sires were heterozygous. All genotyped offspring (n=60) were either GC or CC.

Based on the results above, it was concluded that death of GG homozygous embryo occur at the first few days after fertilization.

The lethality of GG homozygote in cattle was further confirmed by an experiment using IVF embryos. The inventor produced more than 300 IFV embryos using a GC sire and GC cows, or a GC sire and CC cows. Specifically, semen samples were obtained from seven bulls currently used in artificial insemination (AI) in the U.S., and their STAT5A gene genotyped. A bull that was found to be heterozygous (CG) was selected for the experiment. Oocytes were aspirated from 21 heterozygous (CG) and homozygous (CC) cows and fertilized with semen obtained from the heterozygous bull. Survival rate of the embryos was measured at days 7-9. It was found that embryos from the GC.times.CC parents had a survival rate about 19% higher than that from the CG.times.CG parents. Genotyping the survived embryos revealed that all embryos were either CC or CG. When degenerative embryos (those that did not survive beyond day 5 or 6) were genotyped, it was found that GG genotype was present, indicating that the GG genotype leads to early embryo degeneration.

The present inventors further tested the correlation between genotypes of the lethal gene and occurrence of pregnancy of Holstein heifers. Heifers is an ideal population to early out this experiment compared to lactating cows because in lactating cows, genetic factors affecting pregnancy are believed to be diluted with many other environmental factors which makes it hard to detect these genetic factors. In contrast, heifers have consistently higher pregnancy rates than lactating cows and any small increase is of great economic importance. Records were collected of 623 inseminations between different bulls and cows. As shown in Table 2 below, the results were in agreement with previous results obtained in the IVF experiments.

TABLE 2

Pregnancy Frequency Heifers of Different Genotypes

| | Frequency of pregnancy | |
|---|---|---|
| | OPEN | PREGNANT |
| CC genotype | 0.34 | 0.66 |
| GC genotype | 0.45 | 0.55 |

Pregnancy rate was 66% in cows carrying genotype CC versus 55% in cows carrying genotype GC. This the first field experiment that confirms lab results.

The cattle and pig STAT5A proteins have 96% identity at the amino acid level, and the identity between sheep and pig STAT5 proteins is 92%. Because of this high similarity (see Table 1, supra), similar roles the protein plays in various organisms (Development 130, 5257-5268 (2003)) and its evolutionary history, a GG homozygote, or a similar SNP, in other animals, especially other mammals also have lethal effects on the embryos.

Based on the above results, the present invention provides, in one embodiment, a method for increasing the reproductive performance of an mammal population, the method comprising determining the identity of the nucleotide, on both copies of the chromosome, at or corresponding to position 7480 of exon 8 of the bovine STAT5A gene, and eliminating animals having a heterozygous CG genotype as a breeding parent. As discussed above, while a GG homozygote cannot survive in the adult animal population, a GC heterozygote will survive and be present in the population. GC heterozygous animals, however, are not ideal candidates as parents in a breeding program because about 25% of progenies from such parents will be of the GG genotype and will not survive.

Accordingly, the present invention provides a nucleic acid based genetic marker for identifying a lethality allele. This marker can be used for genotyping an animal and for selecting an animal for breeding purposes.

In another embodiment, the present invention provides a method for selecting a mammal as a parent, wherein the mammal is genotyped as described above, and selected as a breeder only if the animal is homozygous CC.

In another embodiment, the present invention can be used to find markers that are in strong linkage disequilibrium with the SNP corresponding to position 7480 of the bovine STAT5A gene. These strongly linked markers can be used as a substitute for the described marker. The present invention also provides, in a preferred embodiment, polymorphisms or polymorphic sites that are in linkage disequilibrium with the SNP corresponding to position 7480 of the bovine STAT5A gene. Linkage refers to the phenomenon that DNA sequences closely adjacent to each other in the genome, specifically, on a chromosome in eukaryotes, have a tendency to be inherited together. Typically, two polymorphic sequences are co-inherited because of the relative infrequency with which meiotic recombination events occur within the region between the two polymorphisms, often due to physical proximity. Two sequences may also be linked because of some selective advantage of co-inheritance. The co-inherited polymorphic alleles are said to be in linkage disequilibrium with one another because, in a given population, they tend to either both occur together or else not occur at all in any particular member of the population. Where multiple polymorphisms in a given chromosomal region are found to be in linkage disequilibrium with one another, they define a quasi-stable genetic "haplotype." In contrast, if meiotic recombination between two polymorphisms occurs frequently enough, the two polymorphisms will appear to segregate independently and are said to be in linkage equilibrium.

Generally speaking, the frequency of meiotic recombination between two markers is proportional to the physical distance between them on the chromosome. However, there are "hot spots" and regions of repressed chromosomal recombination that cause discrepancies between the physical distance and the so-called "recombinational distance." Consequently, a genetic haplotype could cover a broad region of the chromosome, with multiple polymorphic loci in linkage disequilibrium with one another. Where one mutation or polymorphism is found within or in linkage with this haplotype, another one or more polymorphic alleles of the haplotype can be used as indicators of a phenotype known to be linked to or caused by the mutation. Such correlation can and often are used for prognostic or diagnostic procedures without the identification and isolation of the actual causal genetic factor. This is significant because the precise determination of the molecular nature involved in the genetic cause of the phenotype of interest can be difficult and laborious, and the availability of polymorphic markers in linkage disequilibrium with the phenotype of interest often facilitates in the identification of the genetic causal genetic factor(s).

In another embodiment, the present invention can be used to genotype relatives of the animals of interest. Gene probability theory can then be used to predict the marker genotype of an individual based on marker genotype information from relatives in the population. For instance if an individual animal has CG genotype and its female parent has CC genotype, it will be known with 100% certainty that the male parent has CG genotype without having genotyped that sire for the described marker.

In general, for use as markers, nucleic acid fragments, preferably DNA fragments, will be of at least 10 to 12 nucleotides (nt), preferably at least 15 nt, usually at least 20 nt, often at least 50 nt. Such small DNA fragments are useful as primers for the polymerase chain reaction (PCR), and/or probes for hybridization-based screening.

The present invention also encompasses the complementary sequence corresponding to the polymorphism. In order to provide an unambiguous identification of the specific site of a polymorphism, the numbering of the original sequences in the GenBank is shown in FIG. 1 and is used.

The term primer refers to a single-stranded oligonucleotide capable of acting as a point of initiation of template-directed DNA synthesis under appropriate conditions (i.e., in the presence of four different nucleoside triphosphates and an agent for polymerization, such as, DNA or RNA polymerase or reverse transcriptase) in an appropriate buffer and at a suitable temperature. The appropriate length of a primer depends on the intended use of the primer but typically ranges from 15 to 30 nucleotides. Short primer molecules generally require cooler temperatures to form sufficiently stable hybrid complexes with the template. A primer needs not reflect the exact sequence of the template but must be sufficiently complementary to hybridize with a template. The term primer site, or priming site, refers to the region of the target DNA to which a primer hybridizes. The term primer pair means a set of primers including a 5' upstream primer that hybridizes with the 5' end of the DNA sequence to be amplified and a 3', downstream primer that hybridizes with the complement of the 3' end of the sequence to be amplified.

The term "probe" or "hybridization probe" denotes a defined nucleic acid segment (or nucleotide analog segment) which can be used to identify by hybridization a specific polynucleotide sequence present in samples, the nucleic acid segment comprising a nucleotide sequence complementary of the specific polynucleotide sequence to be identified. "Probes" or "hybridization probes" are nucleic acids capable of binding in a base-specific manner to a complementary strand of nucleic acid.

An objective of genotyping according to the present invention is to determine which embodiment of the polymorphism a specific sample of DNA has. Many detection techniques are available and well-known to those skilled in the art. For example, an oligonucleotide probe can be used for such purpose. Preferably, the oligonucleotide probe will have a detectable label. Experimental conditions can be chosen such that if the sample DNA contains a C at position 7480, then the hybridization signal can be detected because the probe hybridizes to the corresponding complementary DNA strand in the sample, while if the sample DNA contains an G, no hybridization signal is detected.

Similarly, PCR primers and conditions can be devised, whereby the oligonucleotide is used as one of the PCR primers, for analyzing nucleic acids for the presence of a specific sequence. These may be direct amplification of the genomic DNA, or RT-PCR amplification of the mRNA transcript of the genes. Amplification may be used to determine whether a polymorphism is present, by using a primer that is specific for the polymorphism. Alternatively, various methods are known in the art that utilize oligonucleotide ligation as a means of detecting polymorphisms, for examples see Riley et al (1990) Nucleic Acids Res. 18:2887-2890; and Delahunty et al (1996) Am. J. Hum. Genet. 581239-1246. The detection method may also be based on direct DNA sequencing, or hybridization, or a combination thereof. Where large amounts of DNA are available, genomic DNA is used directly. Alternatively, the region of interest is cloned into a suitable vector and grown in sufficient quantity for analysis. The nucleic acid may be amplified by PCR, to provide sufficient amounts for analysis.

Hybridization may be performed in solution, or such hybridization may be performed when either the oligonucleotide probe or the target polynucleotide is covalently or noncovalently affixed to a solid support. Attachment may be mediated, for example, by antibody-antigen interactions, poly-L-Lys, streptavidin or avidin-biotin, salt bridges, hydrophobic interactions, chemical linkages, UV cross-linking baking, etc. Oligonucleotides may be synthesized directly on the solid support or attached to the solid support subsequent to synthesis. Solid-supports suitable for use in detection methods of the invention include substrates made of silicon, glass, plastic, paper and the like, which may be formed, for example, into wells (as in 96-well plates), slides, sheets, membranes, fibers, chips, dishes, and beads. The solid support may be treated, coated or derivatized to facilitate the immobilization of the allele-specific oligonucleotide or target nucleic acid. For screening purposes, hybridization probes of the polymorphic sequences may be used where both forms are present, either in separate reactions, spatially separated on a solid phase matrix, or labeled such that they can be distinguished from each other. Assays may utilize nucleic acids that hybridize to one or more of the described polymorphisms, and may include all or a subset of the polymorphisms listed in Table 1.

Hybridization may also be performed with nucleic acid arrays and subarrays such as described in WO 95/11995. The arrays would contain a battery of allele-specific oligonucleotides representing a plurality of the polymorphic sites. One or both polymorphic forms may be present in the array, for example the polymorphism at position 7480 of the STAT5A gene may be represented. Usually such an array will include at least 2 different polymorphic sequences, i.e. polymorphisms located at unique positions within the locus. Arrays of interest may further comprise sequences, including polymorphisms, of other genetic sequences, particularly other sequences of interest. The oligonucleotide sequence on the array will usually be at least about 12 nt in length, or may extend into the flanking regions to generate fragments of 100 to 200 nt in length. For examples of arrays, see Ramsay (1998) Nat. Biotech. 16:4044; Hacia et al. (1996) Nature Genetics 14:441-447; Lockhart et al. (1996) Nature Biotechnol. 14:1675-1680; and De Risi et al. (1996) Nature Genetics 14:457-460. As well-known to those ordinarily skilled in the art, the presence or absence of hybridization signals, optionally in combination of the signal strength, will determine the presence or absence of which of the alleles, and whether the sample is heterozygous or homozygous in regard to the SNP.

The identity of polymorphisms may also be determined using a mismatch detection technique, including but not limited to the RNase protection method using riboprobes (Winter et al., Proc. Natl. Acad. Sci. USA 82:7575, 1985; Meyers et al., Science 230:1242, 1985) and proteins which recognize nucleotide mismatches, such as the E. coli mutS protein (Modrich, P. Ann. Rev. Genet. 25:229-253, 1991). Alternatively, variant alleles can be identified by single strand conformation polymorphism (SSCP) analysis (Orita et al., Genomics 5:874-879, 1989; Humphries et al., in Molecular Diagnosis of Genetic Diseases, R. Elles, ed., pp. 321-340, 1996) or denaturing gradient gel electrophoresis (DGGE) (Wartell et al., Nucl. Acids Res. 18:2699-2706, 1990; Sheffield et al., Proc. Natl. Acad. Sci. USA 86:232-236, 1989).

A polymerase-mediated primer extension method may also be used to identify the polymorphism(s). Several such methods have been described in the patent and scientific literature and include the "Genetic Bit Analysis" method (WO 92/15712) and the ligase/polymerase mediated genetic bit analysis (U.S. Pat. No. 5,679,524). Related methods are disclosed in WO 91/02087, WO 90/09455, WO 95/17676, U.S. Pat. Nos. 5,302,509, and 5,945,283. Extended primers containing a polymorphism may be detected by mass spectrometry as described in U.S. Pat. No. 5,605,798. Another primer extension method is allele-specific PCR (Ruao et al., Nucl. Acids Res. 17:8392, 1989; Ruao et al., Nucl. Acids Res. 19, 6877-6882, 1991; WO 93/22456; Turki et al., J. Clin. Invest. 95:1635-1641, 1995). In addition, multiple polymorphic sites may be investigated by simultaneously amplifying multiple regions of the nucleic acid using sets of allele-specific primers as described in Wallace et al. (WO 89/10414).

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2', 4',7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}P$, $^{35}S$, $^{3}H$; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

It is readily recognized by those ordinarily skilled in the art that in order to maximize the signal to noise ratio, in probe hybridization detection procedure, the polymorphic site should be at the center of the probe fragment used, whereby a mismatch has a maximum effect on destabilizing the hybrid molecule; and in a PCR detection procedure, the polymorphic site should be placed at the very 3'-end of the primer, whereby a mismatch has the maximum effect on preventing a chain elongation reaction by the DNA polymerase. The location of nucleotides in a polynucleotide with respect to the center of the polynucleotide is described herein in the following manner. When a polynucleotide has an odd number of nucleotides, the nucleotide at an equal distance from the 3' and 5' ends of the polynucleotide is considered to be "at the center" of the polynucleotide, and any nucleotide immediately adjacent to the nucleotide at the center, or the nucleotide at the center itself is considered to be "within 1 nucleotide of the center." With an odd number of nucleotides in a polynucleotide any of the five nucleotides positions in the middle of the polynucleotide would be considered to be within 2 nucleotides of the center, and so on. When a polynucleotide has an even number of nucleotides, there would be a bond and not a nucleotide at the center of the polynucleotide. Thus, either of the two central nucleotides would be considered to be "within 1 nucleotide of the center" and any of the four nucleotides in the middle of the polynucleotide would be considered to be "within 2 nucleotides of the center," and so on.

Alternatively, the relevant portion of the relevant genetic locus of the sample of interest may be amplified via PCR and directly sequenced. It is readily recognized that numerous other primers can be devised based on the sequence of Accession No. AJ 237937 such as those shown in FIG. 1. PCR and sequencing techniques are well known in the art and reagents and equipments are readily available commercially. The identity of the polymorphic site in the amplified fragment may also identified by RFLP, according to method and techniques well-known to those skilled in the art.

Alternatively, an invasive signal amplification assay, as described in e.g. U.S. Pat. No. 5,422,253 and Lyamichev et al., 2000, Biochemistry 39:9523-9532, both incorporated herein by reference in their entirety, may be used for detecting the SNP of interest. This assay takes advantage of enzymes such as the 5' nuclease activity of a DNA polymerase or the gene 6 product from bacteriophage T7 in their ability to cleave polynucleotide molecules by recognizing specific structures instead of specific sequences. A single-stranded target molecule is annealed to a pilot oligonucleotide such that the 5' end of the pilot forms a duplex with the target molecule. If the 3' end of the pilot oligonucleotide does not pair with the target, a 3' arm is formed. When exposed to a cleavage agent such as a DNA polymerase having a 5' nuclease activity or the gene 6 product from bacteriophage T7, the target molecule is cleaved in the 5' region, one nucleotide into the duplex adjacent to the unpaired region of the target. If a cut in a double-stranded molecule is required, the double-stranded molecule is denatured. Because this unpaired 3' arm can be as short as one nucleotide, this assay can be used for detecting a single-nucleotide difference, e.g. in the context of SNP detection. The pilot oligonucleotide is designed such that it pairs perfectly with one allele, but has a 3', single nucleotide mismatch with another allele. Cleavage only occurs if there is a mismatch between the target molecule and the pilot. To achieve signal amplification, the above invasive reaction is modified such that cleavage occurs on the pilot oligonucleotide. Two oligonucleotides are annealed in an adjacent manner to the target molecule. The resulting adjacent duplexes overlaps by at least one nucleotide to create an efficient substrate, called the overlapping substrate, for the 5' nucleases. The 5' end of the downstream oligonucleotide, also called the probe, contains an unpaired region termed the 5' arm (Lyamichev et al., 1993, Science 260:778-783.) or flap (Harrington and Lieber, 1994, EMBO J 13: 1235-1246) that is not required for the enzyme activity; however, very long arms can inhibit cleavage (Lyamichev et al., 1993, Science 260:778-783). Specific cleavage of the probe, termed invasive cleavage (Lyamichev et al., 1999, Nat. Biotechnol 17: 292-296; Kwiatkowski et al., 1999, Mol. Diagn. 4, 353-364.), occurs at the position defined by the 3' end of the upstream oligonucleotide, which displaces or "invades" the probe. If the overlap between the adjacent oligonucleotides is only one nucleotide, cleavage takes place between the first two base pairs of the probe, thus releasing its 5' arm and one nucleotide of the base paired region (Lyamichev et al., 1999, Proc. Natl. Acad. Sci. U.S.A. 96: 6143-6148, and Kaiser et al., 1999, J. Biol. Chem. 274: 21387-21394). If the upstream oligonucleotide and the probe are present in large molar excess over the target nucleic acid, and invasive cleavage is carried out near the melting temperature of the probe, a cut probe can rapidly dissociate, and an intact probe will anneal to the target more frequently than will a cut probe, thus initiating a new cycle of cleavage. This allows multiple probes to be cut for each target molecule under isothermal conditions, resulting in linear signal amplification with respect to target concentration and time (Lyamichev et al., 1999, Nat. Biotechnol. 17 292-296).

The present invention further provides a method for genotyping the SATA5A gene of an animal, especially a mammalian, or an individual of an avian or aquatic species, the method comprising determining the nucleotide identity for the two copies of the genetic locus. One embodiment of a genotyping method of the invention involves examining both copies of the genes or coding sequence of STAT5A, or a fragment thereof, to identify the nucleotide pair at the polymorphic site in the two copies to assign a genotype to the individual. In some embodiments, "examining a gene" may include examining one or more of DNA containing the gene, mRNA transcripts thereof, or cDNA copies thereof. As will be readily understood by the skilled artisan, the two "copies" of a gene, mRNA or cDNA, or fragment thereof in an individual may be the same allele or may be different alleles.

In another embodiment, a genotyping method of the invention comprises determining the identity of the nucleotide pair at the polymorphic site.

The present invention further provides a kit for detecting the SNP of the present invention or for genotyping a sample, the kit comprising in a container a nucleic acid molecule, as described above, designed for detecting the polymorphism, and optionally at least another component for carrying out such detection. Preferably, a kit comprises at least two oligonucleotides packaged in the same or separate containers. The kit may also contain other components such as instructional materials and reagents (e.g. hybridization buffer where the oligonucleotides are to be used as a probe and/or enzymes for PCR or RFLP) packaged in a separate container. Alternatively, where the oligonucleotides are to be used to amplify a target region, the kit may contain, preferably packaged in separate containers, a polymerase and a reaction buffer optimized for primer extension mediated by the polymerase, such as PCR.

In another embodiment the present invention provides an animal breeding method whereby genotyping as described above is conducted on animal embryos, and based on the results, certain embryos are either selected or removed from the breeding program. In a preferred embodiment, where CG parent(s) are not avoidable, the present invention provides a selective breeding method which takes advantage of multiple ovulation and embryo transfer procedure (MOET). The method comprises superovulating a female animal, collecting eggs from said superovulated female, in vitro fertilizing said eggs using semen from a suitable male animal, implanting said fertilized eggs into suitable females allowing for an embryo to develop, and determining the SNP of the developing embryo as described above. For animals other than dairy cattle, embryos other than homozygous CC are not transplanted or the pregnancy terminated depending on the circumstances. For dairy cattle, embryos other than CG genotype are not transplanted.

In another embodiment the present invention provides an animal breeding method whereby genotyping as described above is conducted on elite cows (cows to produce bulls), and based on the results, certain elite cows are either selected or not selected to produce the next generation of breeding bulls (young bulls). This makes it possible to break any linkage of the non-lethal allele with lower performance characteristics that may otherwise be present.

In another embodiment, the present invention provides a method for selecting a gamete donor in human assisted reproduction. Assisted reproductive technologies (ART) include IVF (in vitro Fertilization and embryo transfer), GIFT (gamete intrafallopian transfer) and ZIFT (zygote intrafallopian transfer). A fertilized egg is transferred in ZIFT at the pronuclear stage, i.e., prior to the first cell division. The fertilized egg undergoes the first cell division generally at about 30 hours after fertilization, and becomes an embryo. The earliest stage embryo, generally up to four days after fertilization, and up to the 8-cell stage, is referred to as blastomere. From this point on, the embryo is referred to as a morula, and is a solid mass of cells. Approximately 5-6 days after fertilization, the embryo becomes a blastocyst which is a hollow ball of cells, filled with fluid. Embryo hatching and implantation follow.

When a gamete (egg or sperm) donor is needed, the candidates are genotyped and only those who are CC homozygous with regard to the STAT5A SNP of the present invention are selected, thereby eliminating the generation of GG embryos that will subsequently perish.

In the context of human ART, often one of the parents has a CG heterozygous genotype. The present invention provides a method and relevant compositions that can be used to screen in vitro embryos for planting in the uterus, increasing the rate of success while diminishing the chance of multiple pregnancy. A naturally conceived embryo remains in the fallopian tube for 4 days before entering the uterus and implanting on or about day 6. Ideally embryos created through IVF should therefore be transferred on Day 5. However for the last 10 years IVF embryos transferred on Day 5, after being cultured in conventional growth media, had lower implantation rates than those transferred on Day 3. For this reason the practice has been to transfer embryos into the uterus on Day 3. Implantation rates for Day 3 embryos, however, are still only 15% to 20%. To achieve respectable pregnancy rates 3 or more embryos must therefore be transferred whenever possible. This unfortunately dramatically increases the incidence of multiple pregnancies, which is the main criticism against IVF. Currently the ability to accurately identify day 3 embryos that would survive and implant from those that would not is lacking.

According to another embodiment of the present invention, a method is provided for selecting early stage embryos for transfer, such that embryos that cannot survive, i.e. GG homozygotes, are not selected or transferred. This will ensure a high success rate, which would lead to avoidance of transfer of large numbers of embryos and multiple pregnancy, which is the main criticism of ART.

Pre-implantation genetic diagnosis (PGD) techniques are well known to those ordinarily skilled in the art and are frequently used to test embryos for genetic disorders before it implants in the uterus. Typically, a single cell is removed from an 8-cell embryo through an opening in the outer protective coat. The procedure is carried out under the microscope without damaging the embryo's ability to continue to develop normally (because at this stage of development none of the embryo cells have become specialized). The cell is then analyzed for the presence of genetic disorders.

The present invention further discovered, surprisingly, that dairy cattle with heterozygous CG genotype has increased milk yield and higher milk fat and protein yield. Specifics of the experiments that lead to this discovery are discussed below.

Populations and Phenotypic Data:

Blood samples were obtained from the University of Wisconsin (UW) daughter design resource population (henceforth: UW resource population). This population has been investigated to search for genetic markers in association with susceptibility to *mycobacterium tuberculosis*. The 12 sire families of this population were chosen from a large number of candidate bulls with large numbers of daughters in production in 2000. Blood samples from the bulls' daughters have been collected through cooperation with commercial dairy producers throughout the U.S. since January 2001. Yield deviation data for the UW resource populations for milk yield (kg), milk protein and fat yields (kg), were obtained from the USDA Animal Improvement Programs Laboratory (Beltsville, Md.). Summary statistics of these data for milk production traits are given in Table 3.

TABLE 3

Means, standard deviations (SD), minimum, and maximum yield deviations (YD) of cows in the UW resource population for the production traits
University of Wisconsin resource population

| Trait | Mean (Kg) | SD | Min | Max |
|---|---|---|---|---|
| Milk YD | 1092.6 | 1815.1 | −5917 | 7344 |
| Fat YD | 29.97 | 68.17 | −277 | 322 |
| Protein YD | 29.86 | 48.73 | −159 | 181 |

Polymorphism Detection and Genotyping:

Genomic DNA was extracted from blood samples using GFX Genomic Blood DNA Purification Kit (Amersham Biosciences, Piscataway, N.J.). DNA concentration was measured using a spectrophotometer (Ultraspec 2100; Amersham Biosciences). Amplification was performed in a 25 .mu.l reaction volume, which included 50 ng genomic DNA, 50 ng each primer, 200 .mu.M each dNTP, 2.5 .mu.l 10.times. PCR buffer (Promega, Madison, Wis.), and 0.3 u Tag DNA polymerase (Promega). The temperature cycles were as follows: 95.degree. C. for 5 min, followed by 30 cycles of 94.degree. C. for 45 s, touchdown annealing from 65-50.degree. C. for 45 s (−2.degree. C./cycle), 72.degree. C. for 45 s, and a final extension at 72.degree. C. for 7 min. For individual genotyping, primers STAT7 and STAT8 were used to amplify 50 ng genomic DNA and the PCR products were digested with the restriction enzyme BstII that distinguishes alleles C and G of the SNP. The digestion products were electrophoresed on a 1.5% agarose gel.

Statistical Analysis:

Sires and their daughters are genotyped, and phenotypic data was available for the daughters. The linear model used was $$Y_{ijk} = \mu + \text{genotype}_i + \text{sire}_j + \text{Map} + e_{ijk}$$

where $Y_{ijk}$ is the yield deviation (milk, fat, protein) of daughter k, $\mu$ is the mean, $\text{genotype}_i$ is the effect of genotype i, $\text{sire}_j$ is the sire j effect, Map is M. paratuberculosis infection status (noninfected=0, infected=1), and $e_{ijk}$ is the residual.

The results are shown in Table 4 below:

TABLE 4

Estimates of the effects of CG genotypes, standard errors (SE) and P-values for milk production traits (kg) as a deviation from the effect of the genotype (CC) in the UW resource population

| Genotype | Milk yield ± SE (P) | Fat yield ± SE (P) | Protein yield ± SE (P) |
|---|---|---|---|
| CG | 445.9 ± 179.4 (0.0133) | 14.53 ± 7.00 (0.0386) | 9.65 ± 4.86 (0.073) |

Table 4 shows the estimates of the genotype effects for milk yield, protein and fat yield in the UW resource population. Compared to genotype CC, genotype CG was associated with a significant increase in milk yield (445.9 Kg), fat yield (14.53 Kg) and protein yield (9.65 Kg).

Accordingly, in another embodiment, the present invention provides a method of improving dairy cattle breeding. Specifically, because an ideal genotype for a milk-producing cow is CG, for both survivability and production traits, a natural mating between two CC parents is not desirable. Because a GG parent does not exist, CC.times.GG (which would produce 100% CG progeny) is not possible. Thus, parents should be selected for CG.times.CG matings or CC.times.CG matings. Both give 50% CG progeny, and 25% CC. CC.times.CG matings are particularly preferred because it is more desirable for the remaining 25% of the resultant embryos to have a CC genotype, than 25% GG for them to have genotype which will die at very early stages of the embryo development, which will occur in a CG.times.CG mating. In addition, CC.times.CG mating is preferred because milk production traits may be otherwise compensated by additional genetic traits.

In situations where there are more control, for example in in vitro fertilization and embryo transfer, the present invention further provides a method of selecting parents (CG), such that fertilization occurs between CC.times.CG or CG.times.CG parents, in combination with a step to deselect CC embryos (poor production traits) and GG embryos (early embryo death), so that only CG embryos are planted.

The foregoing description and examples have been set forth merely to illustrate the invention and are not intended to be limiting. Since modifications of the disclosed embodiments incorporating the spirit and substance of the invention may occur to persons skilled in the art, the invention should be construed broadly to include all variations falling within the scope of the appended claims and equivalents thereof. All references cited hereinabove and/or listed below are hereby expressly incorporated by reference.

What is claimed is:

1. A method for selectively breeding bovine animals, the method comprising:
   obtaining a nucleic acid sample from a bovine animal;
   detecting, in said nucleic acid sample, the presence of CC homozygous content in the STAT5A gene at position 700 of SEQ ID NO: 3; and
   breeding the bovine animal.

2. The method of claim 1, wherein said breeding uses both male and female bovine animals that are CC homozygous in the STAT5A gene at position 700 of SEQ ID NO: 3.

3. The method of claim 2, wherein said breeding comprises in vitro fertilization of a female bovine animal.

4. The method of claim 1, wherein said breeding comprises use of the bovine animal as a gamete donor for natural mating, artificial insemination, in vitro fertilization, or in a multiple ovulation and embryo transfer procedure.

5. The method of claim 4, wherein a male gamete donor and a female gamete donor used in said natural mating, artificial insemination, in vitro fertilization, or in a multiple ovulation and embryo transfer procedure are both CC homozygous in the STAT5A gene at position 700 of SEQ ID NO: 3.

* * * * *